US00PP19217P2

(12) United States Plant Patent
Baker et al.

(10) Patent No.: US PP19,217 P2
(45) Date of Patent: Sep. 16, 2008

(54) ***COLEUS ×PERILLA* PLANT NAMED 'GAGE'S SHADOW'**

(50) Latin Name: *Solenostemon scutellariodes×Perilla frutescens*
Varietal Denomination: Gage's Shadow

(76) Inventors: Cheryl Baker, 2546 Alabama Highway 117, Mentone, AL (US) 35984; David Baker, 2546 Alabama Highway 117, Mentone, AL (US) 35984; Gage Baker, 2546 Alabama Highway 117, Mentone, AL (US) 35984; Robert Baker, 2546 Alabama Highway 117, Mentone, AL (US) 35984

( * ) Notice: Subject to any disclaimer, the term of this patent is extended or adjusted under 35 U.S.C. 154(b) by 0 days.

(21) Appl. No.: 11/800,785

(22) Filed: May 7, 2007

(51) Int. Cl.
*A01H 5/00* (2006.01)

(52) U.S. Cl. ..... Plt./373
(58) Field of Classification Search ..... Plt./373
See application file for complete search history.

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct cultivar of *Coleus X Perilla* plant named 'Gage's Shadow', characterized by its upright and uniform growth habit; vigorous growth habit; freely branching habit; and green and dark purple-colored leaves.

1 Drawing Sheet

Botanical designation: *Solenostemon scutellarioides×Perilla frutescens.*
Cultivar denomination: 'Gages's Shadow'.

BACKGROUND OF THE INVENTION

The present invention relates to a new and distinct cultivar of *Coleus X Perilla*, botanically known as *Solenostemon scutellarioides×Perilla frutescens* and hereinafter referred to by the name 'Gage's Shadow'.

The new *Coleus X Perilla* is a product of a planned breeding program conducted by the Inventors in Mentone, Ala. The objective of the breeding program is to create new *Coleus X Perilla* cultivars with attractive leaf coloration.

The new *Coleus X Perilla* originated from a cross-pollination during the spring of 2001 in Mentone, Ala. of the *Solenostemon scutellarioides* cultivar Felix, not patented, as the female, or seed, parent with the *Perilla frutescens* cultivar Magilla, not patented, as the male, or pollen, parent. The new Coleus X Perilla was discovered and selected by the Inventors as a single flowering plant within the progeny of the stated cross-pollination in a controlled environment in Mentone, Ala. during the summer of 2001.

Asexual reproduction of the new *Coleus X Perilla* by terminal cuttings in a controlled environment in Mentone, Ala. since the autumn of 2001, has shown that the unique features of this new *Coleus X Perilla* are stable and reproduced true to type in successive generations.

SUMMARY OF THE INVENTION

The cultivar Gage's Shadow has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Gage's Shadow'. These characteristics in combination distinguish 'Gage's Shadow' as a new and distinct cultivar of *Coleus X Perilla:*

1. Upright and uniform growth habit.
2. Vigorous growth habit.
3. Freely branching habit.
4. Green and dark purple-colored leaves.

Plants of the new *Coleus X Perilla* differ from plants of the female parent, the cultivar Felix, in the following characteristics:

1. Plants of the new *Coleus X Perilla* are taller than plants of the cultivar Felix.
2. Plants of the new *Coleus X Perilla* have larger leaves than plants of the cultivar Felix.
3. Plants of the new *Coleus X Perilla* and the cultivar Felix differ in leaf coloration as plants of the cultivar Felix have burgundy-colored leaves.

Plants of the new *Coleus X Perilla differ from plants of the male parent, the cultivar Magilla, in the following characteristics:*

1. Plants of the new *Coleus X Perilla* and the cultivar Magilla differ in stem color.
2. Plants of the new *Coleus X Perilla* have larger leaves than plants of the cultivar Magilla.
3. Plants of the new *Coleus X Perilla* and the cultivar Magilla differ in leaf coloration as plants of the cultivar Magilla have purple, green and pink-colored leaves.

Plants of the new *Coleus X Perilla* can be compared to plants of the Coleus cultivar Velvet Lime, not patented. In side-by-side comparisons conducted by the Inventors in Mentone, Ala. plants of the new *Coleus X Perilla* differed from plants of the cultivar Velvet Lime in the following characteristics:

1. Plants of the new *Coleus X Perilla* were taller than plants of the cultivar Velvet Lime.
2. Plants of the new *Coleus X Perilla* had larger leaves than plants of the cultivar Velvet Lime.

3. Plants of the new *Coleus X Perilla* and the cultivar Velvet Lime differed in leaf color as plants of the cultivar Velvet Lime had burgundy-colored leaves with green margins.

BRIEF DESCRIPTION OF THE PHOTOGRAPHS

The accompanying colored photographs illustrate the overall appearance of the new *Coleus X Perilla*, showing the colors as true as it is reasonably possible to obtain in colored reproductions of this type. Colors in the photographs may differ slightly from the color values cited in the detailed botanical description which accurately describe the colors of the new *Coleus X Perilla.*

The photograph at the bottom of the sheet comprises a side perspective view of a typical plant of 'Gage's Shadow' grown in a container.

The photograph at the top of the sheet is a close-up view of typical leaves of 'Gage's Shadow'.

DETAILED BOTANICAL DESCRIPTION

The aforementioned photographs and following observations, measurements and values describe plants grown in Bonsall, Calif. in containers in a shaded polyethylene-covered greenhouse during the summer and under conditions which closely approximate commercial production. During the production of the plants, day temperatures ranged from about 16° C. to 35° C. and night temperatures ranged from about 13° C. to 18° C. Plants were pinched one time and were about seven weeks old when the photographs and the description were taken. In the description, color references are made to The Royal Horticultural Society Colour Chart, 1995 Edition, except where general terms of ordinary dictionary significance are used.

Botanical classification: *Solenostemon scutellarioides*× *Perilla frutescens* cultivar Gage's Shadow.

Parentage:

*Female, or seed, parent.*—*Solenostemon scutellarioides* cultivar Felix, not patented.

*Male, or pollen, parent.*—*Perilla frutescens* cultivar Magilla, not patented.

Propagation:

*Type.*—By terminal cuttings.

*Time to initiate roots, summer.*—About six days at 29° C.

*Time to initiate roots, winter.*—About nine days at 24° C.

*Time to produce a rooted young plant, summer.*—About 10 to 16 days at 29° C.

*Time to produce a rooted young plant, winter.*—About 16 to 20 days at 18° C.

*Root description.*—Fine, fibrous.

*Rooting habit.*—Freely branching; moderately dense.

Plant description:

*Plant and growth habit.*—Upright and uniform growth habit; inverted triangle. Vigorous growth habit. Freely branching; about eight lateral branches develop per plant.

*Plant height.*—About 35 cm.

*Plant diameter.*—About 52 cm.

Lateral branch description:

*Length.*—About 30 cm.

*Diameter.*—About 8 mm.

*Internode length.*—About 5 cm to 6 cm.

*Strength.*—Strong.

*Aspect.*—Mostly upright.

*Texture.*—Smooth, glabrous.

*Color.*—79A.

Foliage description:

*Arrangement.*—Opposite, simple.

*Length.*—About 8 cm.

*Width.*—About 5.8 cm.

*Shape.*—Elliptic to slightly deltoid.

*Apex.*—Acute to acuminate.

*Base.*—Attenuate.

*Margin.*—Crenate.

*Texture, upper surface.*—Sparsely pubescent.

*Texture, lower surface.*—Smooth, glabrous.

*Venation pattern.*—Pinnate; arcuate.

*Color.*—Developing foliage, upper surface: 146A; venation, 79B. Developing foliage, lower surface: 146B; venation, 79B. Fully expanded foliage, upper surface: Mostly 79A with scattered mottled patches of 147A; venation, 79B. Fully expanded foliage, lower surface: Darker than 79A; venation, 79A.

*Petiole length.*—About 4.2 mm.

*Petiole diameter.*—About 2 mm.

*Petiole texture, upper surface.*—Sparsely pubescent.

*Petiole texture, lower surface.*—Smooth, glabrous.

*Petiole color, upper and lower surfaces.*—79A.

Flower description: Flower development has not been observed.

Pathogen/pest resistance: Plants of the new *Coleus X Perilla* have not been observed to be resistant to pests and pathogens common to *Coleus X Perilla.*

Garden performance: Plants of the new *Coleus X Perilla* have been observed to tolerate wind and rain and have good garden performance.

Temperature tolerance: Plants of the new *Coleus X Perilla* have been observed to tolerate temperatures from about 5° C. to about 35° C.

It is claimed:

1. A new and distinct *Coleus X Perilla* plant named 'Gage's Shadow' as illustrated and described.

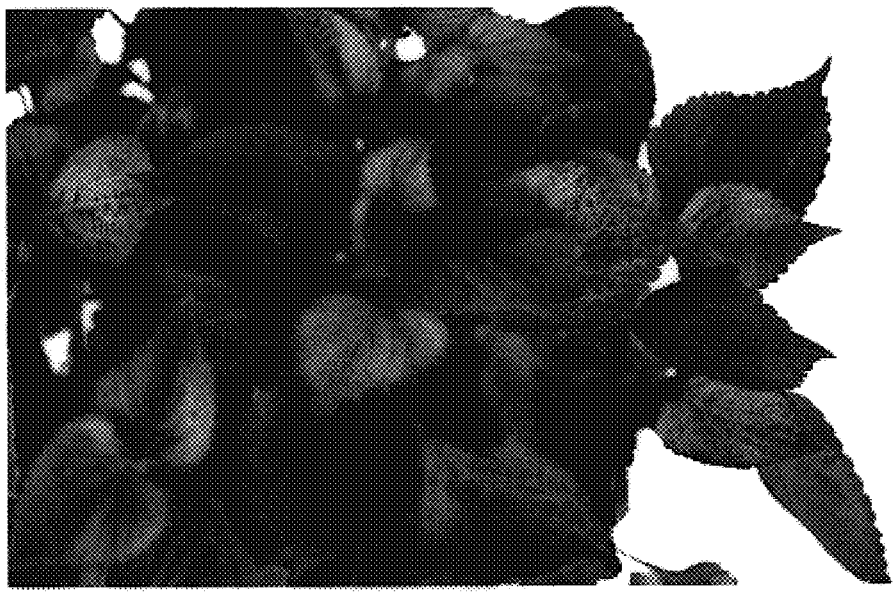
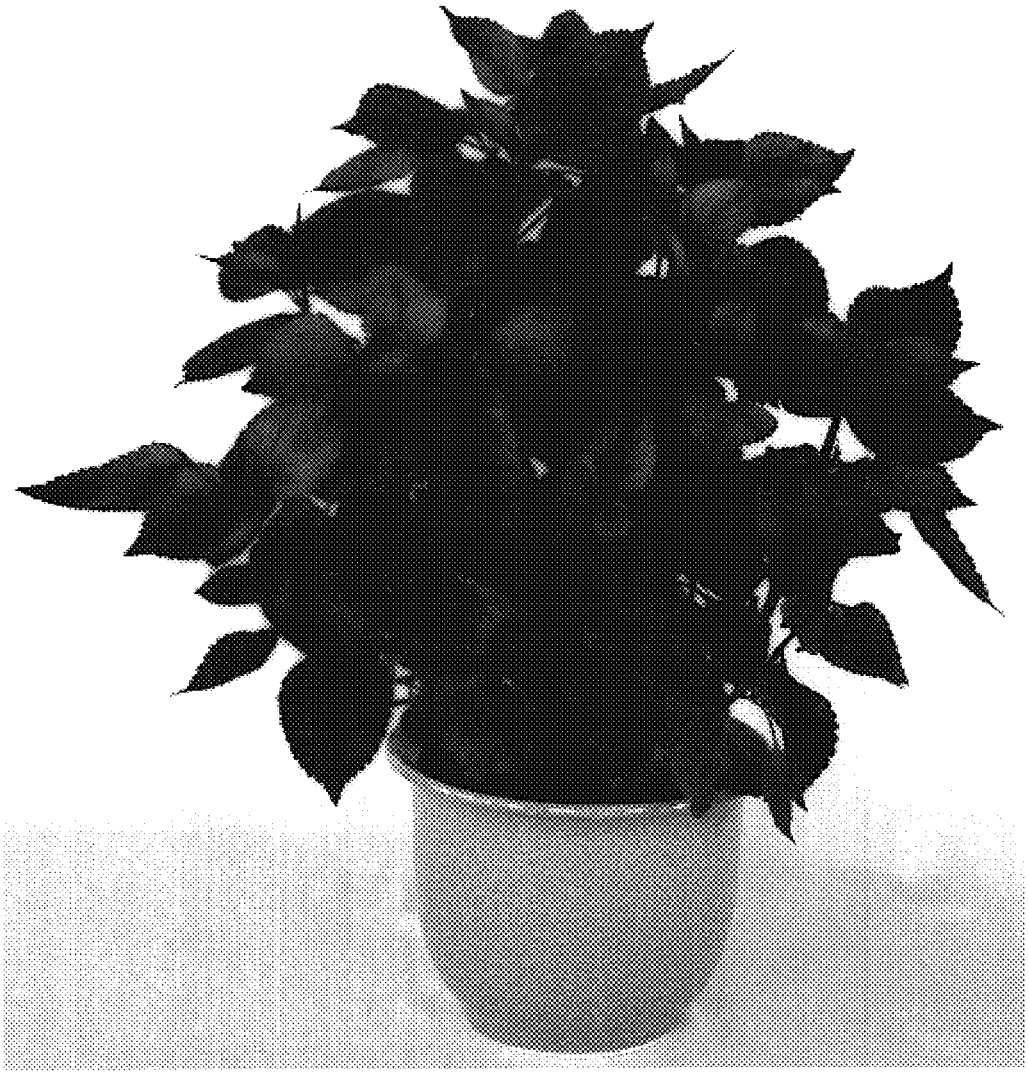

* * * * *